(12) United States Patent
Eyal et al.

(10) Patent No.: US 6,171,501 B1
(45) Date of Patent: Jan. 9, 2001

(54) PROCESS FOR THE SEPARATION OF AMINO ACIDS AND THEIR SALTS FROM AN AQUEOUS SOLUTION

(75) Inventors: Aharon Meir Eyal; Nadjda Cohen-Sydov, both of Jerusalem (IL)

(73) Assignee: Yissum Research Development Company of the University of Jerusalem, Jerusalem (IL)

(*) Notice: Under 35 U.S.C. 154(b), the term of this patent shall be extended for 0 days.

(21) Appl. No.: 09/214,710

(22) PCT Filed: Jul. 11, 1997

(86) PCT No.: PCT/GB97/01874

§ 371 Date: Feb. 10, 1999

§ 102(e) Date: Feb. 10, 1999

(87) PCT Pub. No.: WO98/02411

PCT Pub. Date: Jan. 22, 1998

(30) Foreign Application Priority Data

Jul. 15, 1996 (IL) ........................................ 118855

(51) Int. Cl.$^7$ ................................................ C07C 227/40
(52) U.S. Cl. ......................... 210/634; 210/639; 562/554
(58) Field of Search ............................ 562/554; 210/634, 210/639

(56) References Cited

U.S. PATENT DOCUMENTS 4,334,095 * 6/1982 Baniel .
4,661,606 * 4/1987 Tuominen et al. .

OTHER PUBLICATIONS

Wen Shiuh Kuo et al., Recovery of Glutamic Acid from Fermentation Broth by Membrane Processing, J. of Food Sci. vol. 52, No. 5, 1987, pp. 1401–1404.
Ko Aida, An Overview of the Microbial Production of Amino Acids, Progr. Ind. Micr., vol. 24, 1986, pp. xxi–xxvi.
G.A. Yagodin et al., Liquid Membrane Extraction of Aminoacids, ISEC'86, vol. III, 1986, pp. 677–683.
P. Deblay et al., Separation of $_L$–Valine from Fermentation Broths Using A Supported Liquid Membrane, Biotech. and Bioeng., vol. 35, 1990, pp. 123–131.
H. Itoh et al., A Liquid Emulsion Membrane Process for the Separation of Amino Acids, Biotech. and Bioeng., vol. 35, 1990, pp. 853–860.
R.T. Morrison et al., *Organic Chemistry*, 1975, pp. 1136–1137.
R. Haensel et al., Reactive Extraction of d, I–Phenylalanine With Trioctyl–Methyl–Ammonium Chloride (Tomac) As A Carrier–III. Equilibrium And Mass Transfer Investigations, Chem. Eng. Sci., vol. 41, No. 7, 1986, pp. 1811–1815.
V.F. Selemenev et al., Interaction of Glutamic Acid with the AV–17–2P Anion Exchanger, Russ. Journal. Phys. Chem., vol. 58, No. 10, 1984, pp. 1531–1533.
V.F. Selemenev et al., Absorption of Glutamic Acid by Sulphonic Acid Cation Exchangers, Russ. Journal. Phys. Chem., vol. 59, 1985, pp. 1178–1180.
K. Schügerl, et al., Recovery of Low–Molecular Organic Compounds From Complex Aqueous Mixtures by Extraction, Chem. Ing. Tech., vol. 61, No. 10, pp. 796–804.
Aharon M. Eyal et al., Extraction of Metal Salts by Mixtures of Water–Immiscible Amines and Organic Acids (Acid–Base Couple Extractants). 1. A Review of Distribution and Spectroscopic Data and of Proposed Extraction Mechanisms, Ind. Eng. Chem. Res., vol. 33, No. 5, 1994, pp. 1067–1075.
Aharon M. Eyal, Acid Extraction by Acid–Base Coupled Extractants, Ion Exchange and Solvent Extraction, vol. 13, pp. 31–93.

* cited by examiner

*Primary Examiner*—Gary Geist
*Assistant Examiner*—Leigh C. Maier
(74) *Attorney, Agent, or Firm*—Foley & Lardner

(57) ABSTRACT

The invention provides a process for the separation of amino acids and their salts from impurities contained in an aqueous feed solution containing the same, the process comprising: a) bringing the feed solution into contact with a substantially immiscible extractant phase comprising an amine and an acid, both of which are substantially water immiscible in both free and salt forms, to extract amino acid and salts thereof in the phase, wherein the extraction is carried out while the feed solution is within two pH units of the initial pH of the feed solution; and b) backwashing the extractant phase with a substantially neutral aqueous system to recover substantially all of the extracted amino acid and the extracted salts thereof.

13 Claims, No Drawings

PROCESS FOR THE SEPARATION OF AMINO ACIDS AND THEIR SALTS FROM AN AQUEOUS SOLUTION

This application is a 371 of PCT/GB97/01874, filed Jul. 11, 1997.

The present invention relates to a process for the separation of amino acids and their salts from impurities contained in an aqueous solution containing the same.

In recent years all over the world there has been a noticeable growth of amino acid utilization. Amino acids find their commercial application in human food, animal feed additives and in the pharmaceutical field. They are also used as intermediates for syntheses in special chemicals like synthetic sweeteners, chelating agents and pharmaceutical peptides (see e.g. Maui K. N., Chiao G. C., Chlauda F. P. "Recovery of Carboxylic and Amino Acids via Membrane Water Splitting", AICHE Annual Meeting in Los Angeles, Calif. (1991); and Wen Shiuh Kuo, Been Huang Chiang "Recovery of Glutamic Acid from Fermentation Broth by Membrane Processing", J. of Food Sci. Vol. 52, No. 5, p. 1401, (1987)).

Most amino acids are industrially produced by fermentation (see e.g. Aika K. Chibata I., Nakayama K., Takinami K., Yamada H. "Biotechnology of Amino Acids Production" Progr. Ind. Micr., Vol. 24 p. xxi, (1986)). These fermentation liquors are very complex and contain a great amount of fermentation byproducts, which increase the complexity and the cost of amino acid recovery and purification. These costs may reach up to 20% of the total production cost (See e.g. Yagodin G. A., Yrtov E. V., Golubcov A. S. "Liquid Membrane Extraction of Amino Acids" ISEC'86, Vol. III, p. 685, (1986)).

At present, a succession of filtrations, crystallization and redissolution, complicated ion-exchange steps and numerous steps of concentration are necessary (see e.g. Dablay P., Minier M., Renon H. "Separation of L-Valine from Fermentation Broths Using a Supported liquid Membrane", Biotech. and Bioeng., Vol. 35, p. 123, (1990)). In many of the separations chemical energy application as a driving force results in consumption of reagents and in production of by-product salts of low or negative value. In search of more simple and less expensive way of amino acid separation from fermentation broth, liquid-liquid extraction was suggested. This separation method is based on amino acid properties to change the ionic charge depending on pH of the media (see e.g. Itoh H., Thien M. P., Wang D. I. C. "A Liquid Emulsion Membrane Process for the Separation of Amino Acids" Biotech. and Bioeng., Vol. 35, p. 853 (1990)).

Bearing amino and carboxylic groups, amino acids can be readily turned into cations, anions or zwitterions through pH changes as described by Morrison R. T., Boyd R. N. "Organic Chemistry" PP. 1136–1137, Boston, (1975)., and in accordance with the following reaction scheme:

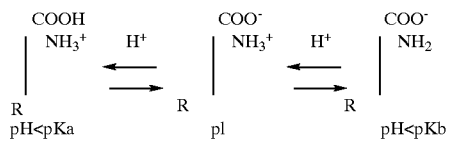

For phenylalanine, for example, pKa=1.83 pI=5.48 and pKa$_2$=9.15, wherein pI is the isoelectric point
Therefore, amino acids can exist as cations or anions or zwitterions. Two types of extractants acting as ion exchangers have been reported to be applicable in amino acid extraction systems (see e.g. Itoh I., Thien M. P., Hatton T. A., Wang D. I. C. "A Liquid Emulsion membrane Process for the Separation of Amino Acids" Biotech. and Bioeng. Vol. 35 pp. 853–854, (1990)). The first one is positively charge lipophilic extractant, such as Aliquat 336, a quaternary ammonium salt. The second one is a negatively charged extractant, such as di (2-ethyl-hexyl)phosphoric acid (D2EHPA), a lipophilic acid. Both ionic extractants are complexed with counter ions to maintain electro-neutrality in the apolar organic phase. These counter ions can be exchanged with charged amino acid solute of the same charge at the aqueous phase/organic interphase by an interfacial ion-exchange reaction to form an extractant amino acid complex The newly formed complex then diffuses across the organic phase. The amino acid containing organic phase can be stripped by an aqueous solution of an electrolyte, an acid or a base. At the stripping phase/organic interphase another ion exchange reaction takes place. The counter-ion in the stripping phase is exchanged for the amino acid which is then released into the stripping phase.

For Phe (phenylalanine) extraction from synthetic aqueous solution (see e.g. Haensel R., Halwachs W., Schugerl K. "Reactive Extraction of l,d-Phenylalanine with Tri-Octyl-Methyl-Ammonium Chloride (TOMAC) as a Carrier-III Equilibrium and Mass Transfer Investigations" Chem. Eng. Sci., Vol. 41, No. 7., pp. 1812–1813 (1986)) Phe was transformed into an anion by addition of NaOH to achieve equilibrium pH=11. The initial concentration of Phe was $C_{in}$=16.9 g/l. The extractant, 2.5 M TOMAC (tri-octylmethylammonium chloride) in xylene, was taken with phase ration 1:1. The extraction coefficient was K=5.2 and the extraction proceeded according to the following reaction:

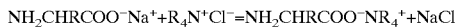

It was also shown that Trp (Tryptophane) extraction by 0.15 M TOMAC in xylene is more efficient than Tyr (Tyrosine) extraction by the same extractant. (The tests were made in single amino acids systems). Initial aqueous amino acid solutions of nearly equal concentrations $C_{Trp}$=10.2 g/l, $C_{Tyr}$=9.05 g/l were treated with NaOH solution to obtain amino acid anions (pH=11). Extraction coefficients were $K_{Trp}$=10, $K_{Tyr}$=1.1 [10]. The extraction selectivity of Asp (Aspartic acid) and Arg (Arginine) in extraction by TOMAC was also studied at high pH (see e.g. Schugerl K., Degener W., "Gewinung Midermolekularer Organischer Verbindungen aus Komlexen Wasrigen Gemishen durch Extraction" Chem. -Ing. -Tech. Vol. 61, No. 10, p. 798 (1989)).

0.0726 M D2EHPA in benzene was used as cation exchanger in Phe extraction (see e.g. Teramoto M., Miyake Y., Matsuyama H., Nara H. "Extraction of amino acids with Organophosphorus Extractant" Solvent Extr., pp. 1803–1808, (1990)). At equilibrium pH=4.2 distribution coefficients were for Phe 0.015
Trp 0.014
Val 0.005 (Valine)
Ala 0.006 (Alanine)
Gly 0.0004 (Glycine
Lys 1.41 (Lysine)

For industrial separation of several amino acids (Phe, Glu, Asp, Trip, Tyr, etc.) from their fermentation broths, quarternary ammonium extractants were suggested (see e.g. U.S. Pat. No. 4,661,606.)

Resins are other kinds of ion exchangers, studied for amino acid separation. Ion exchange resins are synthetic resins having a chemical structure based on a cross linked three-dimensional polymer molecule onto which functional groups such as sulfonic acid and quartemary ammonium are bound. Ion exchange reactions are carried out combined with a diffusion of counter ions out of the resin particles. The ion exchange mechanism is similar to that of extraction by liquid ion exchangers. For anion exchange of Glu (Glutamic acid), quaternary ammonium resin AV172p in OH⁻ form with resin capacity of about 3 mg-equiv.g⁻¹ was taken (see e.g. Selemenev V. F., Oros G. Yu., Ogneva L. A., Trubetskich G. V., Chikin G. A. "Interaction of Glutamic Acid with the AV-17-2P Anion Exchanger." Russ. J. of Phys. Chem., Vol. 58 (10), pp. 1531–1532, (1984)). Glu with initial concentration $C_{in}$=7.46 g/l was converted into the anion form at initial pH=7.7. The distribution coefficient D was 1 with phase volume ratio $V_{solution}/V_{resin}$=400. In cation form (see e.g. Selemenev V. F., Miroshnikova Z. P., Ogveva L. A., Ermakova I. I., Kotova D. L., Oros G. Yu. "Absorption of Glutamic Acid by Sulphonic Ction Exchangers" Russ. J. of Phys. Chem., Vol. 59 (8), pp. 1178–1180) Glu was absorbed by a sulfonic acid Resin KY-2-8 with D=9.9. So, it is seen that equilibrium distribution coefficients of ion exchange by extraction and by resins are comparable and their values are close. Nevertheless extraction process has two important advantages over ion exchange resins: a) it is several times faster, and b) it does not entail dilutions due to sweetening off.

To shift the pH to an acidic [or basic] range one needs to add some acid [or base] into the solution and this leads to additional byproducts. Furthermore, at such a low (or high) pH only strong ion exchangers can work. Also for amino acid stripping, in these cases a base [or an acid] must be consumed. Better extractants can be very helpful in solving the problem of amino acid separation from fermentation broth.

In accordance with the present invention it has now been surprisingly found that acid base couple extractants (hereinafter ABC extractants), can be effectively utilized for the separation of amino acids and their salts from impurities contained in an aqueous solution containing the same, and in preferred embodiments of the present invention there is provided a process for the separation of amino acids and their salts from impurities contained in an aqueous feed solution containing the same, wherein said feed solution is obtained from a fermentation process.

More particularly, the present invention provides a process for the separation of amino acids and their salts from impurities contained in an aqueous feed solution containing the same, wherein said solution has a pH value of pH>pI, in the case of acidic amino acids, has a pH value of pH<pI in the case of basic amino acids, and has a pH value of pI−2<pH<pI+3 in the case of neutral amino acids, and wherein pI is the isoelectric point, comprising a) bringing said feed solution into contact with a substantially immiscible extractant phase comprising an amine and an acid, both of which are substantially water immiscible in both free and salt forms to extract amino acid and salts thereof into said phase, wherein said extraction is carried out while said feed solution is within two pH units of the initial pH of said feed solution; and b) backwashing said extractant phase with a substantially neutral aqueous system to recover substantially all of the extracted amino acid and the extracted salts thereof.

In preferred embodiments of the present invention, said process is carried out on a solution which has a pH value of pI<pH<pI+5 in the case of acidic amino acids, a pH value of pI−4<pH<pI in the case of basic amino acids, and a pH value of pI−2<pH<pI+3 in the case of neutral amino acids.

Preferably, said extraction is carried out at a substantially neutral pH in the range of about 4–9.

ABC extractants were studied as extractants for extracting mineral salts such as $MgCl_2$, $ZnSO_4$, LiCl and others from aqueous solution. (A recent review was published by Eyal et. al. in Industrial and Engineering Chemistry Research (1994), 33, 1067–1085.) Baniel suggested application of ABC extractants for extraction of strong acids (European 0017500) and for organic acids (U.S. Pat. No. 4,334,095). Several processes based on extraction of mineral acids by ABC extractants were proposed (European 0083831, U.S. Pat. No. 4,439,408 and others, (see the recent review by Eyal published in Ion Exchange and Solvent Extraction, Vol.13).

Extraction of mineral salts and of acids by ABC extractants was studied extensively in the last two decades and is now understood quite well. In the case of the mineral salts extraction, the cation of the salt is bound by the water immiscible acid that acts as a liquid cation exchanger, and the anion of the salt is bound to the amine, that acts as a liquid anion exchanger. In the case of extracting an acid (mineral or carboxylic), the binding is to the amine and the water immiscible acid does not play a role in the extraction step. It does facilitate the back-extraction. Based on these mechanisms, the extraction of amino acids from neutral solutions seem quite surprising due to the adjacent amino and carboxylic groups.

Amino acids are in the zwitterionic form in solutions, the pH of which is at about the isoelectric point (pi). Thus, at about neutral solutions, in neutral amino acids (5<pI<7) both the amine group and the carboxylic groups are charged and form a strong intramolecular bond. Liquid anion or cation exchangers are expected to be too weak to open this bond. Even if they do, that would not lead to introduction of the amino acid into the organic phase (extraction) as the neutrality would not be maintained, which is why extraction by liquid cation exchangers or liquid anion exchangers works only at high pH or low pH respectively, where the other charge is removed Analysis of mineral salts extraction by ABC extractants view in some cases the ABC extractant as being a salt of the amine ($R'_nNH_{(4-n)}$) and the water immiscible acid (HA). However, one would not expect that an ABC would, by analogy to the quatemary amine salt, form a neutral adduct of the type $R(NH_3A)COOR'_nNH_{(4-n)}$. The expectation would be that, due to the large size of the extractant components, there would be no room for fitting the two large complexes $NH_3A$, and $COOR'_nNH_{(4-n)}$ on the same carbon atom, particularly if the amine is not a straight chain fatty acid. It was surprisingly found that the extraction does take place with ABC extractants comprising bulky amines such as primary amines where the nitrogen group is on a tertiary carbon atom ($R'_3CNH_2$), secondary, tertiary and quatemary amines, by those comprising bulky diesters of phosphoric acid or dinonyinaphthalenesulfonic acid and by ABC extractants comprising combinations of bulky amines and organic acids.

Another, and even more surprising finding was that extraction was feasible using ABC extractants comprising relatively weak amine and/or acid, e.g., with non-quartemary amines and with water immiscible acids that are non-sulfonic ones. The amine group of the neutral amino acids is quite a strong base and its pKa in most cases is >9. In order to displace it from the zwitterion with the carboxylic acid of the amino acid (to bind the latter to the amine), the amine of the ABC extractant should be of at least the same strength. Yet, the basicity of water immiscible non-quatemary amines is much lower, pka's of about 7, 5 and 3 for primary, secondary and tertiary amines respectively (Grinstead and Davis J. Phys. Chem. (1968), 72, 1630–38). Using the same logic, the HA that binds to the amino group of the amino acid should be stronger than the carboxylic group of the neutral amino acids. The latter have pKa of about 2 which make them quite strong acids. Dialkyl esters of phosphoric acid and even more so, fatty acids, are weaker acids and would not be expected to be able to displace such carboxylic groups from the binding to the amino group.

Some of these difficulties are avoided in the extraction of acidic or basic amino acids. In aqueous solution of about neutral pH those are in the salt form. In that sense their extraction could be considered more similar to that of mineral salts. However, one would also not expect an extraction where the cationic or anionic amino acid binds to the HA, or to amine, respectively, and the conjugated ion to the other component of the ABC extractant. Such extraction is expected to be difficult due to the need to introduce the highly hydrophilic zwitterion (in the zwitterionic form as present at neutral medium), into the extractant. (Binding of anionic or the cationic amino acid in the charged form to solid ion is known, but there the medium in which the bonded ion resides is aqueous.) This difficulty is demonstrated in the numerous studies of extracting amino acid in their zwitterion into organic solvents. The extraction of alkali metal and ammonium salts of acidic amino acids would be even less expected, as even the mineral salts of these cations are hardly extracted by ABC extractants. Surprisingly, it was found that salts such as lysine chloride and sodium glutamate are extracted by ABC extractants, and in preferred embodiments of the present invention said amino acid salt, which is recovered is selected from the group consisting of monosodium glutamate, ammonium aspartate and lysine hydrochloride.

Especially preferred acids are organic acids for the extractant selected from the group consisting of alpha-, beta- and gamma-chloro and bromo substituted carboxylic acids, diesters of phosphoric acids and fatty acids, e.g. alpha-bromo lauric acid, beta-, beta-dichloro decanoic acid and gamma dibromo octanoic acid, diethylhexyl phosphoric acid (DEHPA), lauric acid, etc.

The amines are preferably primary, secondary and tertiary amines, singly or in mixtures, and characterized by having at least ten (10) and preferably at least fourteen (14) carbon atoms. Such commercially available amines as Primene JM-5, and Primene JM-T (which are primary aliphatic amines in which the nitrogen atom is bonded directly to a tertiary carbon atom), and which commercial amines are sold by Rohm and Haas Chemical Co., Amberlite LA-1 and Amberlite LA-2, which are secondary amines sold by Rohm and Haas, Alamine 336, a tertiary tricaprylyl amine (TCA) sold by Henkel, Aliquat 336, methyl tricaprylyl amine sold by Henkel, and Alamine 304 a tertiary trilaurylamine (TLA) sold by Henkel can be used in the processes of the present invention, as well as other well-known and available amines, including e.g., those secondary and tertiary amines listed in U.S. Pat. No. 3,458,282. Especially preferred for the use in the present invention is an amine selected from the group consisting of trilaurylamine (TLA), methyl tricaprylyl amine and tricaprylyl amine (TCA).

In preferred embodiments of the present invention the molar ratio of said acid to said amine in the extractant is between about 0.5 to 1 and 1 to 0.5.

The extractant phase can further comprise a diluent or solvent chosen from a wide range of organic liquids known to persons skilled in the art, which can serve as solvents for said acid-amine active components and which provide for greater ease in handling and extracting control. Said carrier solvents can be unsubstituted or substituted hydrocarbon solvents in which the organic acid and amine are known to be soluble, and which are substantially water insoluble, e.g., kerosene, mineral spirits, naphtha, benzene, xylene, toluene, nitrobenzene, carbon tetrachloride chloroform, trichloroethylene, etc. Also, higher oxygenated compounds such as alcohols, ketones, esters, ethers, etc., that may confer better homogeneity and fluidity, and others that are not acids or amines, but which may confer an operationally useful characteristic, can also be included.

Being a mixture of liquid anion exchanger and liquid cation exchanger, these extractants extract the amino acids and their salts, while avoiding major changes in the acidity of the aqueous phase. Acid or base consumption for pH adjustment is avoided. Similarly, recovery of the extracted amino acid or its salt, and regeneration of the extractant are achieved by back-extraction with a substantially neutral aqueous system, preferably at a temperature higher than the temperature of extraction, avoiding the consumption of reagents. Thus, said amino acid is preferably recovered from said aqueous backwashing system by crystallization, and said substantially neutral aqueous system is water.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

An aqueous solution comprising 70 g/L valine is counter-currently extracted at ambient temperature with an extractant composed of tricaprylyl amine (Alamine 336 produced by Henkel), di-2-ethylhexyl phosphoric acid (DEHPA) and octanol in a low-aromatics kerosene. The concentration of the amine and that of DEHPA are 0.5 mol/L each and the octanol is 30% w/w in the extractant. The organic to aqueous phase ratio is 5 to 1 and the number of stages is seven. More than 90% of the valine in the aqueous phase is extracted, yielding an extract (loaded extractant) containing 13.1 g/L valine.

The extractant is counter-currently back-extracted with water at ambient temperature. The aqueous to organic phase ratio is 1 to 2.3 and the number of stages is 5. Most of the extracted acid is back-extracted to yield an aqueous solution of valine at a concentration of 30 g/L.

Example 2

An aqueous solution comprising 2 mols/Kg proline is counter-currently extracted at ambient temperature with an extractant composed of methyl tricaprylyl amine (Aliquat 336 produced by Henkel), DEHPA and octanol in a low-aromatics kerosene. The concentration of the amine and that of DEHPA are 0.5 mol/L each and the octanol is 30% w/w in the extractant. The organic to aqueous phase ratio is 1 to 1 and the number of stages is four. More than 90% of the proline in the aqueous phase is extracted, yielding an extract containing nearly 2 mols/Kg proline.

The extract is counter-currently back-extracted with water at ambient temperature. The aqueous to organic phase ratio is 2 to 1 and the number of stages is four. Practically all of the extracted proline is back-extracted to yield an aqueous solution of proline at a concentration of about 1 mol/Kg.

Example 3

An aqueous solution comprising 2 mols/Kg lysine hydrochloride LysHCl is counter-currently extracted at ambient temperature with an extractant composed of methyl tricaprylyl amine, lauric acid and octanol in a low-aromatics kerosene. The concentration of the amine and that of lauric acid are 0.5 mol/L each and the octanol is 30% w/w in the extractant. The organic to aqueous phase ratio is 3.3 to 1 and the number of stages is five. More than 90% of the LysHCl in the aqueous phase is extracted, yielding an extract containing nearly 0.6 mols/Kg LysHCl.

The extract is counter-currently back-extracted with water at ambient temperature. The aqueous to organic phase ratio is 0.8 to 1 and the number of stages is five. Practically all of the extracted LysHCl is back-extracted to yield an aqueous solution of lysine hydrochloride at a concentration of about 0.75 mol/Kg.

Example 4

An aqueous solution comprising 300 g/Kg monosodium glutamate (MSG) is counter-currently extracted at ambient temperature with an extractant composed of methyl tricaprylyl amine and lauric acid in a low-aromatics kerosene. The concentration of the amine and that of lauric acid are 0.5 mol/L each. The organic to aqueous phase ratio is 2.9 to 1 and the number of stages is five. Two-thirds of the MSG in the aqueous phase is extracted, yielding an extract containing nearly 70 g/Kg MSG.

The extract is counter-currently back-extracted with water at ambient temperature. The aqueous to organic phase ration is 1 to 3 and the number of stages is six Practically all of the extracted MSG is back-extracted to yield an aqueous solution of MSG at a concentration of about 205 g/Kg.

Example 5

An aqueous solution comprising 250 g/Kg betain is counter-currently extracted at ambient temperature with an extractant composed of methyl tricaprylyl amine, lauric acid and octanol in a low-aromatics kerosene. The concentration of the amine and that of lauric acid are 0.5 mol/L each and the octanol is 30% w/w in the extractant. The organic to aqueous phase ratio is 2.7 to 1 and the number of stages is six. More than 90% of the betain in the aqueous phase is extracted, yielding an extract containing nearly 75 g/Kg betain.

The extract is counter-currently back-extracted with water at ambient temperature. The aqueous to organic phase ratio is 1 to 2 and the number of stages is five. More than 90% of the extracted betain is back-extracted to yield an aqueous solution of betain at a concentration of about 150 g/Kg.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the separation of one or more amino acids and their salts from impurities contained in an aqueous feed solution containing the same, wherein said solution has a pH value of pH>pI, in the case of acidic amino acids, has a pH value of pH<pI in the case of basic amino acids, and has a pH value of pI−2<pH<pI+3 in the case of neutral amino acids, and wherein pI is the isoelectric point, comprising
    a) bringing said feed solution into contact with a substantially immiscible extractant phase comprising an amine and an acid, both of which are substantially water immiscible in both free and salt forms to extract one or more amino acid and salts thereof into said phase, wherein said extraction is carried out while said feed solution is within two pH units of the initial pH of said feed solution; and
    b) backwashing said extractant phase with a substantially neutral aqueous system to recover substantially all of the one or more extracted amino acids and the extracted salts thereof.

2. A process according to claim 1, wherein said extraction is carried out at a substantially neutral pH in the range of about 4–9.

3. A process according to claim 1, wherein said solution has a pH value of pI<pH<pI+5 in the case of acidic amino acids, a pH value of pI−4<pH<pI in the case of basic amino acids, and a pH value of pI−2<pH<pI+3 in the case of neutral amino acids.

4. A process according to claim 1, wherein said extraction is carried out while said feed solution is within one pH unit of the initial pH of said feed solution.

5. A process according to claim 1, wherein said acid is selected from the group consisting of an alpha- beta- or gamma-chloro or bromo substituted carboxylic acid, diesters of phosphoric acid and fatty acids.

6. A process according to claim 1, wherein said amine is selected from the group consisting of primary, secondary and tertiary amines having at least 10 carbon atoms.

7. A process according to claim 6, wherein said amine is selected from the group consisting of trilaurylamine (TLA), methyl tricaprylyl amine and tricaprylyl amine (TCA).

8. A process according to claim 1, wherein the molar ratio of said acid to said amine is between about 0.5 to 1 and 1 to 0.5.

9. A process according to claim 1, wherein step b is carried out at a temperature higher than step a.

10. A process according to claim 1, wherein said aqueous feed solution containing said amino acids and their salts is obtained from a fermentation process.

11. A process according to claim 1, wherein said amino acid is recovered from said aqueous backwashing system by crystallization.

12. A process according to claim 1, wherein said substantially neutral aqueous system is water.

13. A process according to claim 1, wherein the amino acid salt which is recovered is selected from the group consisting of monosodium glutamate, ammonium aspartate and lysine hydrochloride.

\* \* \* \* \*